United States Patent [19]

Gerhard et al.

[11] Patent Number: 4,502,162

[45] Date of Patent: Mar. 5, 1985

[54] HAPTIC FOR INTRAOCULAR LENS

[75] Inventors: Gregory J. Gerhard, Seattle; Robert J. Gornstein, Dockton; William M. Graham, Burton; Anilbhai S. Patel, Seattle; John M. Smith, Vashon Island; Wade C. Vaughn, Seattle, all of Wash.

[73] Assignee: CooperVision, Inc., Palo Alto, Calif.

[21] Appl. No.: 539,850

[22] Filed: Oct. 7, 1983

[51] Int. Cl.³ .......................... A61F 1/16; A61F 1/24
[52] U.S. Cl. .................................................... 3/13
[58] Field of Search ........................................ 3/13, 1

[56] References Cited

U.S. PATENT DOCUMENTS

| | | |
|---|---|---|
| 3,971,073 | 7/1976 | Richards et al. ............... 3/13 |
| 3,975,779 | 8/1976 | Richards et al. ............... 3/13 |
| 3,996,626 | 12/1976 | Richards et al. ............... 3/13 |
| 4,012,823 | 3/1977 | Richards ........................... 3/13 |
| 4,014,049 | 3/1977 | Richards et al. ............... 3/13 |
| 4,025,965 | 5/1977 | Siegmund ......................... 3/13 |
| 4,143,427 | 3/1979 | Anis ................................. 3/13 |
| 4,166,293 | 9/1979 | Anis ................................. 3/13 |
| 4,174,543 | 11/1979 | Kelman ........................... 3/13 |
| 4,254,511 | 3/1981 | Chase et al. .................... 3/13 |
| 4,257,130 | 3/1981 | Bayers ............................. 3/13 |
| 4,268,921 | 5/1981 | Kelman ........................... 3/13 |
| 4,285,072 | 8/1981 | Morcher et al. ............... 3/13 |
| 4,304,012 | 12/1981 | Richard .......................... 3/13 |
| 4,316,293 | 2/1982 | Bayers ............................. 3/13 |
| 4,328,595 | 5/1982 | Sheets ............................. 3/13 |
| 4,403,353 | 9/1983 | Tennant .......................... 3/13 |
| 4,418,431 | 12/1983 | Feaster ........................... 3/13 |
| 4,437,194 | 3/1984 | Hahs ............................... 3/13 |

OTHER PUBLICATIONS

American Medical Optics, Model PC-80, Posterior Chamber (Knolle) Intraocular Lenses (Advertisement), American Medical Optics, American Hospital Supply Corp., 1402 East Alton Ave., Irvine, CA 92714 (4 pages), Sep. 1982, 3–13.

Primary Examiner—Ronald L. Frinks
Attorney, Agent, or Firm—Christensen, O'Connor, Johnson & Kindness

[57] ABSTRACT

An intraocular lens four point contact haptics with an asymmetrical cross section. The ends of each of the haptics are contiguously juxtaposed and inserted in a common bore in the periphery of the optic. The legs of each of the haptics spiral outwardly in juxtaposed relationship, separate and extend away from each other to form eye contacting heel and toe portions residing on opposing sides of the inferior-superior axis of the lens. When two such haptics are employed, a wide haptic compression range can be achieved with little differential in compression force.

13 Claims, 4 Drawing Figures

HAPTIC FOR INTRAOCULAR LENS

BACKGROUND OF THE INVENTION

The present invention relates to intraocular lenses and more particularly to improved haptics for intraocular lenses.

Intraocular lenses are employed as replacements for the crystalline lens after either extracapsular or intracapsular surgery for the removal of a cataract. Intraocular lenses are generally of two types, those that are placed in the anterior chamber, i.e., between the iris and the cornea, and those that are placed in the posterior chamber, i.e., behind the iris. Both types of lenses are conventionally employed with a choice between an anterior and a posterior lens being partly dictated by the requirements of the patient and partly dictated by the choice of the physician inserting the lens.

Intraocular lenses normally consist of an optic with two or more haptics that extend generally radially from the optic and include a foot portion that normally seats in the scleral spur for an anterior lens and either in the ciliary sulcus or within the lens capsule for a posterior lens. The optic normally comprises a circular transparent optical lens. The haptic in most lenses is a flexible fiber or filament having at least one end affixed to the lens and having a second portion extending generally radially away from the lens to form a seating foot. Several haptic designs are currently in use, for example, U-shaped loops in which both ends of each loop are connected to the lens and J-shaped loops in which only one end of the loop is affixed to the lens. Generally, when U-shaped or J-shaped haptics are employed, two such haptics are utilized with each lens. The haptics are generally diametrically positioned about the optic.

While the haptics are flexible so that they can be compressed radially inwardly during insertion and so that they exert a slight amount of force on the portion of the eye on which they seat to center the lens on the optical axis of the eye, the force required to compress the haptics radially inwardly increases with increasing compression distance. If the force exerted on the eye exceeds a comfortable level, it can at times cause irritation to the eye. For example, a typical lens constructed in accordance with prior art techniques exhibits a compression force when the haptics are compressed a combined distance of 1.5 millimeters of about 2.0 grams. When the haptics are only slightly compressed, the resistive force exerted by the haptics is much smaller.

This characteristic presents difficulty with respect to the proper and comfortable fitting of a lens in the eyes of various patients which, of course, vary significantly in size. Since it is desirable for the compression force exerted by the haptics to be on the order of 1 gram or less, it has become necessary to vary the diameter of the optic as well as the distance from the optical axis at which the seating foot of the haptic resides when relaxed, in order to minimize the force the haptics exert on eye tissue. This results in the necessity to maintain large inventories of lenses of various sizes in order to have the appropriate lens available at the time of surgery.

Moreover, some prior art haptic designs employ what is referred to as four point contact, again generally using two haptics, each of which have two seating portions that are spaced circumferentially relative to the optic. Using this design, the seating pressure on the eye can be spread over a greater distance thus reducing eye irritation or tenderness. Problems have been encountered with four point contact type lens in achieving equal resistive forces at each of the contact locations.

SUMMARY OF THE INVENTION

The present invention provides an intraocular lens having haptics that overcome the foregoing problems of prior art lenses. The haptics are constructed so that the force required to compress the haptics up to 1.5 millimeters or more remains substantially the same from the relaxed state to the fully compressed state. Moreover, a compression force required by a lens designed in accordance with the present invention can be held to as low as 0.5 grams at a compression distance of 1.5 millimeters. As a consequence, only one size of lens produced in accordance with the present invention can be placed in eyes of different sizes while minimizing the amount of tenderness and irritation caused by insertion of the lenses and yet providing sufficient force to center the lens within the posterior or anterior chamber. The present lens by employing haptics with a special cross-sectional shape also will not vault appreciably, that is move forwardly along the optical axis upon compression, thus eliminating the possibility of endothelial damage. In a preferred embodiment, the haptics are constructed so that four seating regions are provided which when compressed provide equal and balanced compression forces at four seating regions.

An intraocular lens constructed in accordance with the present invention comprises an optic and at least one flexible haptic. The optic has an optical axis and an inferior-superior axis intersecting the optical axis. The optic has at least one haptic receiving channel therein, which extends inwardly from the periphery of the optic and has a longitudinal axis oriented substantially parallel to and offset from the inferior-superior axis. The flexible haptic has first and second ends mounted in the haptic receiving channel in the optic and extends generally outwardly from the channel in the optic. The optic has a first leg joined to the first end, a heel joined to the first leg, a second leg joined to the second end, a bridge and a knee joining the second leg to one end of the bridge, a toe joined to the other end of the bridge, and an arch connecting the heel and the toe. The heel and toe are spaced radially outwardly from the periphery of the optic and comprise the eye contacting portion of the haptic. The toe is positioned on one side of the inferior-superior axis while the heel and knee are positioned on the other side of the inferior-superior axis.

In a preferred embodiment, the first and second legs curve outwardly away from the channel and toward the inferior-superior axis. The legs are also substantially contiguous throughout this curved portion. The bridge is spaced outwardly from the legs and the arch in turn is spaced outwardly relative to the optic from the bridge. The arch preferably curves inwardly toward the optic between the heel and toe to form an inwardly concave portion lying on the inferior-superior axis. This provides haptic separation from the eye between the heel and toe portion as well as providing an indentation onto which a surgical tool can be hooked for haptic compression during surgery. In a most preferred form of the invention, the cross section of the filament from which the haptic is made approximates the shape of a major segment of a circle.

BRIEF DESCRIPTION OF THE DRAWINGS

A better understanding of the present invention can be derived by reading the ensuing specification in conjunction with accompanying drawings wherein.

DETAILED DESCRIPTION OF THE INVENTION

Figure 1:
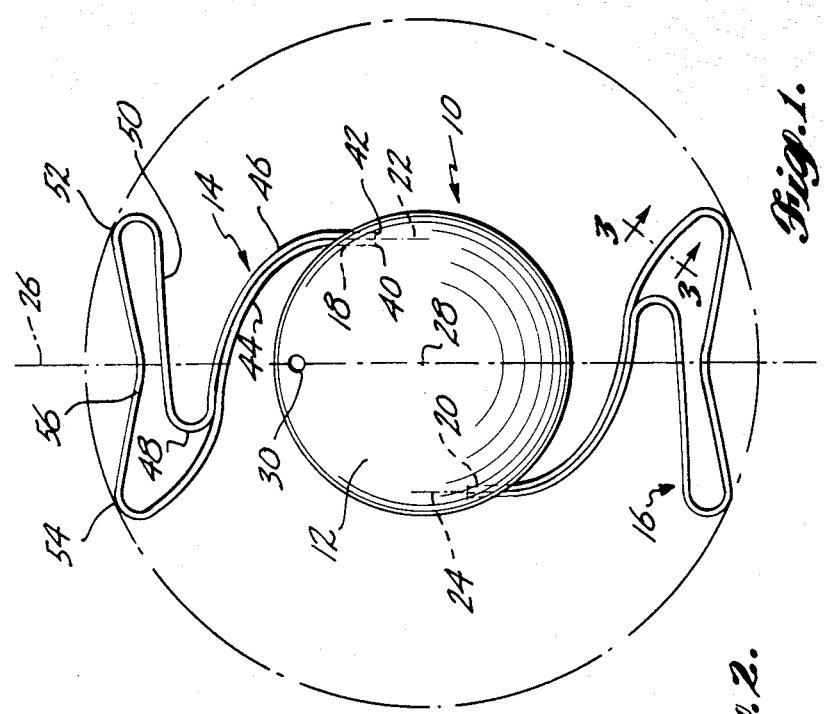
FIG. 1 is a front elevation view of an intraocular lens constructed in accordance with the present invention.
Figure 2:
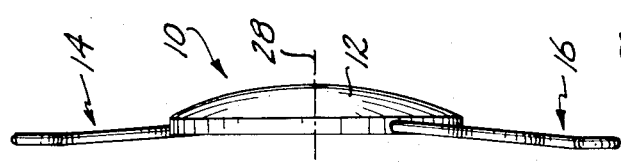
FIG. 2 is a side elevation view of the lens of FIG. 1.

Referring first to FIGS. 1 and 2, an intraocular lens 10 constructed in accordance with the present invention comprises an optic 12 and two haptics 14 and 16. While a variety of optic shapes can be utilized and still take advantage of the present invention, a conventional planoconvex optic 12 is illustrated. The optic is generally circular in configuration, having a planar posterior surface and a convex anterior surface. Optics are generally molded or machined from a clear polymeric material such as polymethylmethacrylate or other biocompatible material.

Two haptic receiving channels 18 and 20 are formed in the optic 12. These channels may be molded when the lens is molded, but are preferably bored during the machining process. Channels 18 and 20 are preferably circular in configuration so as to receive the ends of the haptics 14 and 16 respectively, which when juxtaposed have a cylindrical configuration. Channels 18 and 20 open onto the periphery of the optic 12 and extend inwardly into the optic. The longitudinal axes 22 and 24 of the channels 18 and 20 respectively are oriented substantially parallel to the inferior-superior axis 26 of the lens 10. Channels 18 and 20 are substantially offset from the inferior-superior axis. The longitudinal axes 22 and 24 of the channels intersect a diameter of the optic oriented orthoganally to the inferior-superior axis at a location equalling about 75 percent of the radial distance from the optical axis 28 of the lens to the periphery. Although not forming a part of the invention, a manipulation hole 30 is provided in the optic 12. The manipulation hole is oriented parallel to the optical axis and is positioned adjacent the superior portion of the optic periphery.

Figure 3:
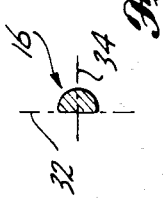
FIG. 3 is a cross-sectional view of the haptic taken along section line 3—3 of FIG. 1.

The key to the improved haptic constructed in accordance with the present invention resides primarily in the haptic configuration when viewed in front elevation, but also derives its superior characteristics at least in part from the cross-sectional shape of the filament from which the haptic is formed. Referring to FIG. 3, the cross-sectional view of the haptic taken along a similar section line 3—3 of FIG. 1 illustrates the most preferred cross-sectional shape to be employed in accordance with the present invention. That shape substantially approximates a major segment of a circle as illustrated. The present invention will, however, function substantially the same when other asymmetrical cross sections are employed. Asymmetrical cross sections that can be employed in accordance with the present invention include those having a major axis 32 and a minor axis 34. The major axis is oriented generally parallel to the optical axis of the lens while the minor axis is generally oriented orthogonally to the major axis. A portion of the cross-sectional area can reside on both sides of the major axis; however, it is currently felt to be important that a substantial portion of the cross-sectional area lie on one side of the axis. Of course, in the currently most preferred cross-sectional shape, virtually all of the cross-sectional area lies on one side of the major axis since the major axis and the diameter of the circle from which the major segment is taken are coincident.

Referring again to FIGS. 1 and 2, the first and second ends 40 and 42 of the haptic 14 are juxtaposed so that the flat sides of the haptic segments are contiguous. Thus, the first and second ends when so juxtaposed form a small cylinder. The haptic receiving channel 18 is sized so that first and second ends 40 and 42 can easily be inserted in the channel. As mentioned earlier, the major axis of the cross section is oriented substantially parallel to the optical axis 28. Both of the first and second ends extend in parallel relationship the full length of the channel 18 and outwardly a short distance from the periphery of the optic. Both the first and second ends are joined to inner and outer legs 44 and 46 that spiral outwardly from the periphery of the optic toward the inferior-superior axis 26. Both of the legs 44 and 46 cross the inferior-superior axis. After crossing the inferior-superior axis, the outer leg 46 circles through an arc of approximately 170° to form a knee 48. The knee 48 transitions into a straight bridge portion 50 that extends back across the inferior-superior axis to join a toe portion 52. The toe again curves through an arc of approximately 190° in an outward direction. The toe 52 forms one of the two eye contacting portions of the first haptic 14.

The inner leg 44 reverses its curvature adjacent the knee 48 and continues to curve outwardly and away from the periphery of the optic 12. The inner leg then transitions into a heel 54, which has an arc with a radius similar to and curvature opposite to that of the toe portion 52. The heel 54 forms the second eye contacting portion of the first haptic 14. The heel 54 and toe 52 are joined by an arch 56. It should be noted at this point that the outermost curved portions of both the heel 54 and the toe 52 are positioned substantially equidistantly from the optical axis 28 of the lens.

The arch 56 joining the heel and the toe, 54 and 52, is chevron shaped with the innermost concave portion of the chevron being positioned across the inferior-superior axis. The convex portion of the arch 56 is spaced outwardly from the bridge portion 50 at the inferior-superior axis. Similarly, the bridge 50 along the inferior-superior axis is spaced outwardly from the inner and outer leg portions 44 and 46 by a distance substantially equal to the distance by which the legs 44 and 46 are spaced from the periphery of the optic 12 at the inferior-superior axis. The distance by which the convex portion of the arch 56 is spaced from the bridge 50 is slightly less than the distance by which the bridge is spaced from the legs 44 and 46.

In order to achieve the unique advantages of the present invention, it is important that the heel and toe 54 and 52 be spaced equidistantly from the optical axis while being positioned on opposite sides of the inferior-superior axis. It is preferred that the knee 48 be positioned on the same side of the inferior-superior axis as the heel, although it is possible for the knee to be moved toward the inferior-superior axis or reside substantially on the inferior-superior axis without creating a large differential in the compressive forces on the heel and toe.

The second haptic 16 is constructed virtually identically to the first haptic 14 with its first and second ends positioned in the haptic receiving channel 20. The legs of the second haptic 16 spiral away from the periphery of the lens in the same counterclockwise direction as the legs 44 and 46 of the first haptic 14. The knee and heel of the second haptic 16 reside on the opposite side of the inferior-superior axis from the knee and heel of the first haptic 14. Similarly, the toe of the second haptic 16 resides on the opposite side of the inferior-superior axis from the toe 52 of the first haptic 14.

Referring to FIG. 2, it should be noted that the haptics 14 and 16 are angled in a posterior direction away from the planar posterior face of the optic 12 as they extend outwardly from the periphery of the optic 12. Angling the haptics in this manner can be accomplished by bending the haptics as they exit from the receiving channels or by forming the receiving channels at the appropriate angle. The outermost ends of the haptic, including the heel and toe portions, are reoriented to reside in a plane that is substantially orthogonally oriented to the optical axis 28. The posterior surface of the planar portions of the heel and toe are referred to as the foot plates.

Figure 4:
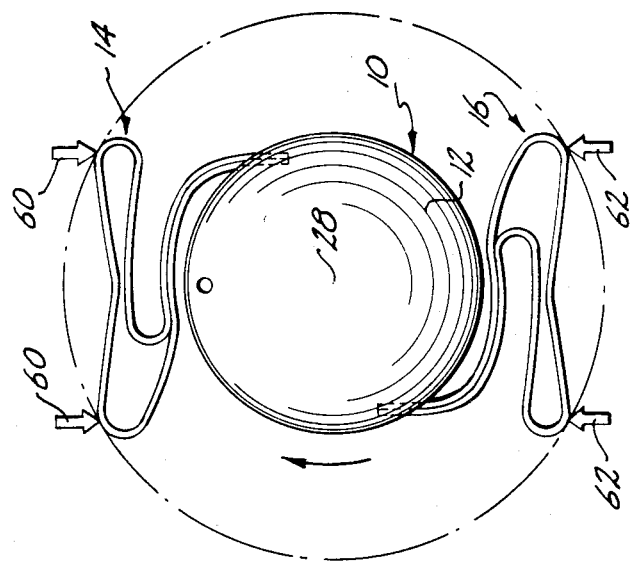
FIG. 4 is a front elevation view of a lens constructed in accordance with the present invention showing the haptics in a compressed state.

A haptic configured in accordance with the present invention can be compressed as shown in FIG. 4 for purposes of accomodating eyes of different sizes. Compression, such as shown in FIG. 4, can also occur upon deformation of the eye as may be caused by an accidental blow. When force is applied to the heel and toe portions of the haptics 14 and 16 either in a generally radial direction or in directions parallel to the inferior-superior axis as represented by arrow 60 and opposing arrow 62, the haptics will compress so that the legs, bridge, and arch all move inwardly along the inferior-superior axis. They are all spaced sufficiently from each other and from the periphery so that the haptics can be compressed to the maximum desirable amount without contact between the periphery and the legs, the legs and the bridge or the bridge and the arch. This coaction prevents interference between the parts and also prevents pinching of eye tissues between the haptic parts. More importantly, however, the force required to compress the haptics toward the optical axis is substantially the same from the fully relaxed position as shown in FIG. 1 to the fully compressed position as shown in FIG. 4. Not only is the sum of the forces applied to one haptic substantially equal to the sum of the forces applied to the other haptic to create equal compression, as importantly, the forces applied to the heel and toe of each haptic are substantially equal. This characteristic of the haptics is created not only by the asymmetrical cross section but also and as importantly by the unique configuration of the haptic. As a consequence, because the forces remain substantially the same over the entire compression range, one size lens can be employed for a variety of eye sizes. Additionally, haptics of the present invention because of their asymmetrical configuration also show little or no tendency to vault. Vaulting is a tendency of the optical lens to move forwardly along the optical axis as the haptics are compressed.

Improved intraocular lenses constructed in accordance with the present invention have been described in relation to a preferred embodiment. One of ordinary skill after reading the foregoing specification will be able to effect various changes, substitutions of equivalents and other alterations to the disclosed embodiment without departing from the broad concepts imparted herein. It is therefore intended that the scope of Letters Patent granted hereon be limited only by the definition contained in the appended claims and equivalents thereof.

The embodiments of the invention in which an exclusive property or privilege is being claimed are defined as follows:

1. An intraocular lens for placement in the eye comprising:

an optic having an optical axis and an inferior-superior axis intersecting said optical axis, said optic having at least one haptic receiving channel therein, said channel extending inwardly from the periphery of said optic and having a longitudinal axis oriented substantially parallel to and offset to one side of said inferior-superior axis, and at least one flexible haptic having first and second ends mounted in said channel and extending outwardly therefrom, said haptic having a first leg joined to said first end, a heel joined to said first leg, a second leg joined to said second end, a bridge and a knee joining said second end to one end of said bridge, a toe joined to the other end of said bridge, and an arch connecting said heel and said toe, said heel and said toe being spaced radially outwardly from the periphery of said optic, said heel and toe being eye contacting portions of said haptic, said toe being on one side of said inferior-superior axis, said heel and knee being positioned on the other side of said inferior-superior axis.

2. The lens of claim 1 wherein said first and second legs curve outwardly away from said channel and toward said inferior-superior axis.

3. The lens of claim 2 wherein said legs are substantially contiguous from said channel to said inferior-superior axis.

4. The lens of claim 3 wherein said arch is spaced outwardly from said bridge.

5. The lens of claim 4 wherein said arch curves inwardly toward said optic from said heel and toe to form a concave portion lying on said inferior-superior axis.

6. The lens of claim 5 wherein said heel and toe are spaced equidistantly from said optical axis.

7. The lens of claim 6 wherein said lens further comprises a second haptic shaped substantially the same as said one haptic and positioned on the opposite side of said optic from said one haptic.

8. The lens of claim 7 wherein the cross-sectional shape of said haptic is asymmetrical and has a major axis and a minor axis, said major axis being substantially parallel to said optical axis.

9. The lens of claim 8 wherein the cross-sectional shape of said haptic approximates a major segment of a circle.

10. The lens of claim 9 wherein the force required to compress said heel and toe of said haptic are substantially equal and remain substantially constant over a substantial portion of the distance over which said heel and toe are compressible.

11. The lens of claim 1 wherein the cross-sectional shape of said haptic is asymmetrical and has a major axis and a minor axis, said major axis being substantially parallel to said optical axis.

12. The lens of claim 11 wherein the cross-sectional shape of said haptic approximates a major segment of a circle.

13. The lens of claim 12 wherein the force required to compress said heel and toe of said haptic toward said optic is substantially equal and remains substantially constant over a substantial portion of the distance over which said heel and toe are compressible.

* * * * *